(12) United States Patent
Mottola et al.

(10) Patent No.: US 8,224,422 B2
(45) Date of Patent: Jul. 17, 2012

(54) ESOPHAGEAL MAPPING CATHETER

(75) Inventors: Brian Mottola, Frisco, TX (US); Martin F. O'Sullivan, Long Beach, CA (US); Sue-Lynn Wu, Brea, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 771 days.

(21) Appl. No.: 11/869,281

(22) Filed: Oct. 9, 2007

(65) Prior Publication Data

US 2008/0177175 A1 Jul. 24, 2008

Related U.S. Application Data

(60) Provisional application No. 60/828,885, filed on Oct. 10, 2006.

(51) Int. Cl.
*A61B 5/05* (2006.01)
(52) U.S. Cl. ......... 600/424; 600/549; 600/593; 606/32; 606/33; 606/34; 607/102; 607/119
(58) Field of Classification Search .................. None
See application file for complete search history.

(56) References Cited

U.S. PATENT DOCUMENTS

| | | | |
|---|---|---|---|
| 5,546,951 A | 8/1996 | Ben-Haim | |
| 5,738,096 A | 4/1998 | Ben-Haim | |
| 6,226,542 B1 | 5/2001 | Reisfeld | |
| 6,266,551 B1 | 7/2001 | Osadchy et al. | |
| 6,368,285 B1 | 4/2002 | Osadchy et al. | |
| 6,650,927 B1 | 11/2003 | Keidar | |
| 2002/0045810 A1* | 4/2002 | Ben-Haim | 600/374 |
| 2002/0120178 A1* | 8/2002 | Tartaglia et al. | 600/114 |
| 2002/0165448 A1* | 11/2002 | Ben-Haim et al. | 600/424 |
| 2003/0069475 A1* | 4/2003 | Banik et al. | 600/152 |
| 2003/0093067 A1* | 5/2003 | Panescu | 606/32 |
| 2004/0242984 A1* | 12/2004 | Plaza | 600/374 |
| 2004/0243011 A1* | 12/2004 | Plaza | 600/509 |
| 2006/0030844 A1 | 2/2006 | Knight et al. | |
| 2006/0106375 A1* | 5/2006 | Werneth et al. | 606/32 |
| 2007/0106289 A1* | 5/2007 | O'Sullivan | 606/41 |

FOREIGN PATENT DOCUMENTS

| | | | |
|---|---|---|---|
| GB | 1203383 | | 8/1970 |
| WO | WO 03/030727 | | 4/2003 |
| WO | WO03/030727 | * | 4/2003 |
| WO | WO 2006/055286 A2 | | 5/2006 |

* cited by examiner

*Primary Examiner* — Long V. Le
*Assistant Examiner* — Bradley Impink
(74) *Attorney, Agent, or Firm* — William A. Schoneman

(57) ABSTRACT

An esophageal mapping catheter enables a physician to map the location of the esophagus so as to avoid damaging the esophagus during radio frequency (RF) ablation procedures. Information from the esophageal mapping catheter is communicated to a patient information unit, communications unit and/or electroanatomic mapping system. The electroanatomic mapping system uses the information from the esophageal mapping catheter to develop a three-dimensional map of the esophagus and to monitor the temperature within the esophagus in order to prevent the creation of esophageal fistula.

4 Claims, 6 Drawing Sheets

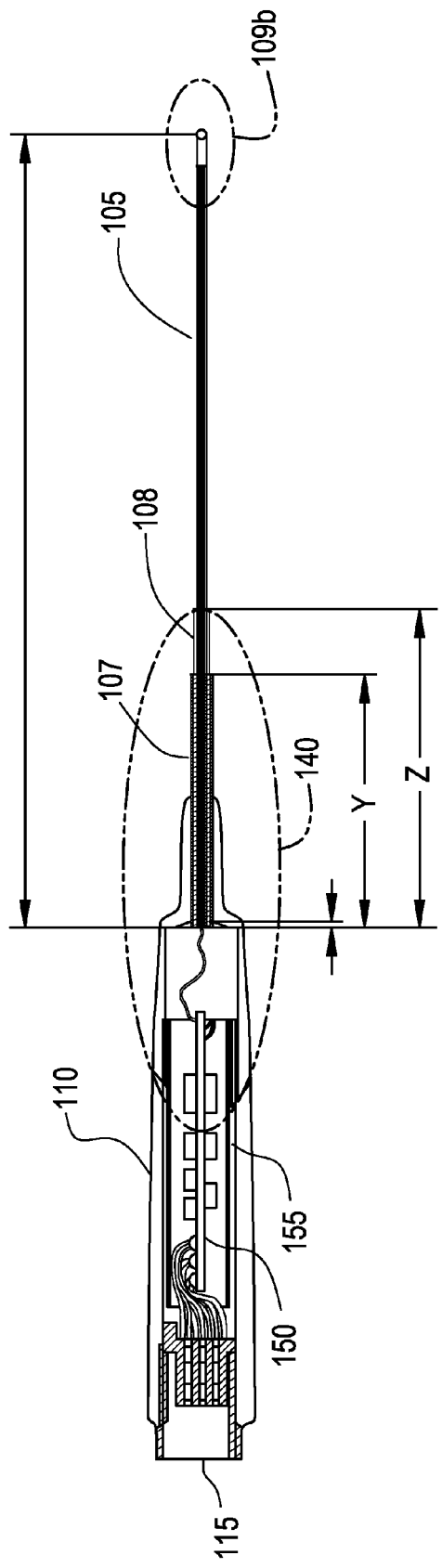
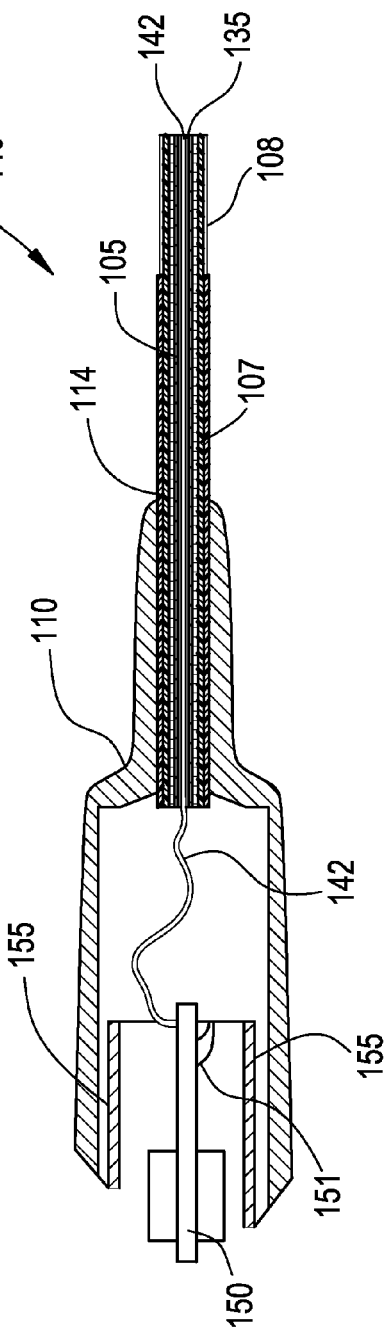

ESOPHAGEAL MAPPING CATHETER

CROSS REFERENCE TO RELATED APPLICATION

This application claims the benefit of U.S. Provisional Application No. 60/828,885, filed Oct. 10, 2006, which is incorporated by reference herein.

FIELD OF THE INVENTION

The present invention relates to a device for catheter-based anatomic mapping of the esophagus for use during an electrophysiology ablation procedure. More particularly, the device is placed in the esophagus via the transpharyngeal or transnasal approach to provide esophagus reference location and orientation data during an ablation procedure.

BACKGROUND OF THE INVENTION

Electrophysiology ablation procedures use energy sources, such as radio frequency (RF) energy, to ablate tissue in order to correct or prevent arrhythmias such as super ventricular tachycardia, paroxysmal atrial tachycardia or atrial fibrillation. Some procedures require the use of the catheter-delivered energy sources near the esophagus resulting in the risk of damage to the esophagus including the creation of esophageal fistula. Due to the proximity of the esophagus to the cardiac atria, it is critical for physicians to know the location of the esophagus during cardiac ablation procedures in the atria in order to minimize the risk of esophageal fistula.

Esophageal fistula associated with ablation used to treat atrial fibrillation have resulted in a high incidence of mortality. The need exists for a device or method to reduce or eliminate the risk of esophageal fistula formation by enabling the electrophysiologist to avoid damaging the esophagus with the energy source used for ablation.

Electroanatomic mapping systems enable a user to develop detailed electroanatomic maps of the heart providing three-dimensional images of the heart to users. Such systems are used to precisely guide ablation catheters to different areas of interest within a heart and can be used to decrease procedure time and reduce exposure to fluoroscopy. One such electroanatomic mapping system is the Carto system produced by Biosense Webster. Such systems that use a catheter to provide three-dimensional location information are described in U.S. Pat. No. 5,546,951 entitled "Method and Apparatus for Studying Cardiac Arrhythmias", U.S. Pat. No. 6,368,285 entitled "Method and Apparatus for Mapping a Chamber of A Heart" and U.S. Pat. No. 6,650,927 entitled "Rendering of Diagnostic Imaging Data on a Three-Dimensional Map" which are hereby incorporated by reference.

Additionally, U.S. Pat. No. 5,738,096, which disclosure is incorporated herein by reference, describes methods for geometrical mapping of the endocardium based on bringing a probe into contact with multiple locations on a wall of the heart, and determining position coordinates of the probe at each of the locations. The position coordinates are combined to form a map of at least a portion of the heart. Once the position of the catheter is known, external sensors can be used to provide local physiological values of heart tissue adjacent to the tip of the catheter.

Further methods for creating a three-dimensional map of the heart based on these data are disclosed, for example, in U.S. Pat. No. 6,226,542, which is assigned to the assignee of the present patent application, and whose disclosure is incorporated herein by reference. Position coordinates (and optionally electrical activity, as well) are initially measured at about 10 to 20 points on the interior surface of the heart. These data points are generally sufficient to generate a preliminary reconstruction or map of the cardiac surface to a satisfactory quality. The preliminary map is preferably combined with data taken at additional points in order to generate a more comprehensive map.

SUMMARY OF THE INVENTION

The present invention generally relates to a catheter-based solution to the above-described problem that provides the user the ability to record and display the location of the esophagus on an electroanatomic mapping system such as the Biosense Webster CARTO™ System. Esophagus location information will enable the user to perform RF ablations in the left atrium such that the esophagus is not in close proximity to the ablation sites, reducing the risk of energy delivery close to the esophagus, thus reducing the risk of esophageal fistula formation.

The esophageal mapping catheter of the current invention includes a flexible, tubular device with a location sensor and thermocouples located in the device tip. The device is introduced into the esophagus via the throat or nasal passage and is aligned behind the heart using fluoroscopic guidance. Prior to performing left atrial (LA) ablations, the physician records location data points within the esophagus by advancing and withdrawing the device within the esophagus while recording catheter location information from the location sensor, tagging location points. The points serve to record device tip position within the esophagus, in turn recording the relative position of the esophagus with respect to the left atrium on the electroanatomic map. Esophagus points displayed on the electroanatomic map enable the physician to direct RF energy delivery away from the esophagus reducing the risk of esophageal fistula formation.

In addition, the device can be placed within the esophagus, behind the left atrium, during RF energy delivery to measure esophagus temperatures. Esophagus temperature changes during ablation may provide the user feedback during the ablation to prevent thermal damage to the esophagus.

The catheter placement in the esophagus can be guided using x-ray to insure that the radiopaque catheter aligns along the posterior wall of the left atrium. The device may be coated with a lubricious material to facilitate easy introduction into and manipulation within the esophagus.

The present invention is a flexible device, suitable for introduction into the esophagus that is instrumented to allow for recording of esophagus position with respect to the ablation site during an electrophysiology ablation procedure. Esophagus position information enables user to direct ablation away from the esophagus reducing risk of esophageal fistula formation. Temperature information may allow the user to control power delivery during ablation to prevent thermal damage to the esophagus.

BRIEF DESCRIPTION OF THE DRAWINGS

FIG. 4 is a longitudinal sectional view of the esophageal mapping catheter of FIG. 2 in accordance with the present invention.

FIG. 5 is a longitudinal sectional view of the transition between the catheter shaft and the handle of the esophageal mapping catheter of FIG. 2 in accordance with the present invention.

DETAILED DESCRIPTION OF THE INVENTION

Figure 1:
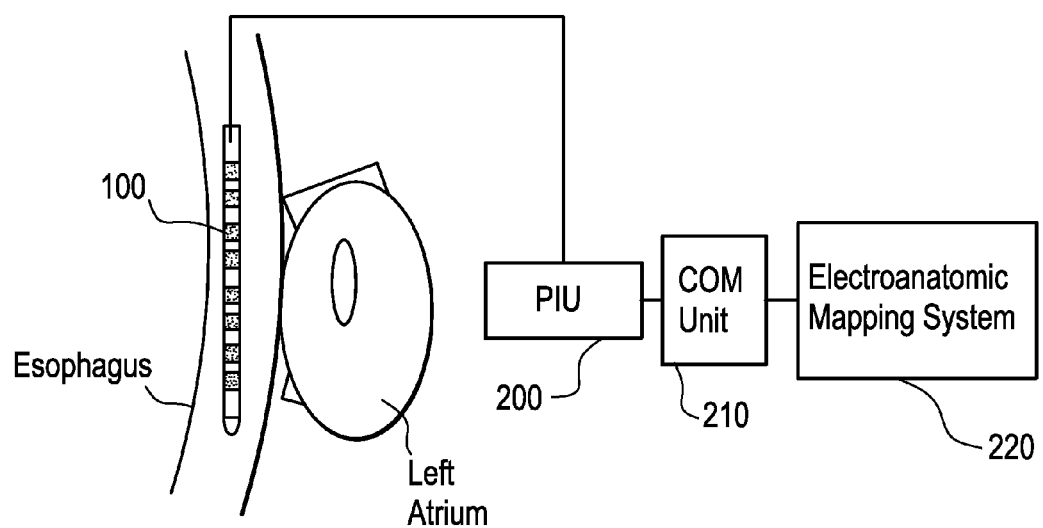
FIG. 1 is a schematic diagram depicting the placement of an esophageal mapping catheter in accordance with the present invention in connection with an electroanatomic mapping system.

FIG. 1 is a diagram depicting the placement of an esophageal mapping catheter 100 in the esophagus near the left atrium of the heart of a patient. Esophageal mapping catheter 100 is electrically connected to the patient interface unit (PIU) 200 in communication with the communications (COM) unit 210 which is further in communication with the electroanatomic mapping system 220. Electrical signals from the esophageal mapping catheter 100 are thereby received and operated upon by the electroanatomic mapping system 220 as described below.

The close anatomical relationship of the posterior wall of the left atrium of the heart and the thermosensitive esophagus, creates a potential hazard in catheter ablation procedures. Esophageal mapping catheter 100 is introduced through the patient's nose or throat into the esophagus. Once in the desired position, the device's location sensor is used to "tag" the 3-D position of the esophagus lumen, using the location software executed in the hardware system that is part of the electroanatomic mapping system 220, as the device is slowly pulled towards the initial entry port.

Figure 2:
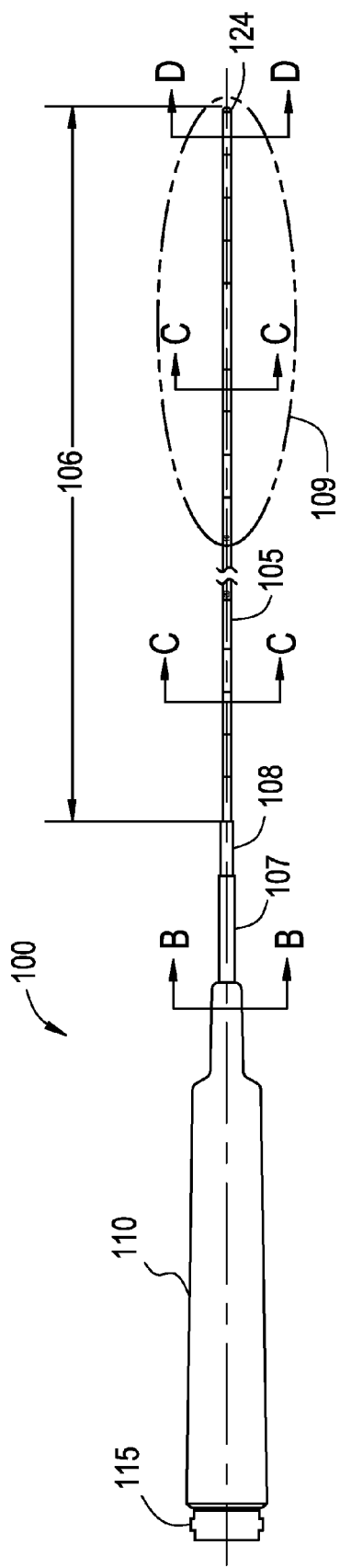
FIG. 2 is an elevational view of an embodiment of an esophageal mapping catheter in accordance with the present invention.
Figure 3:
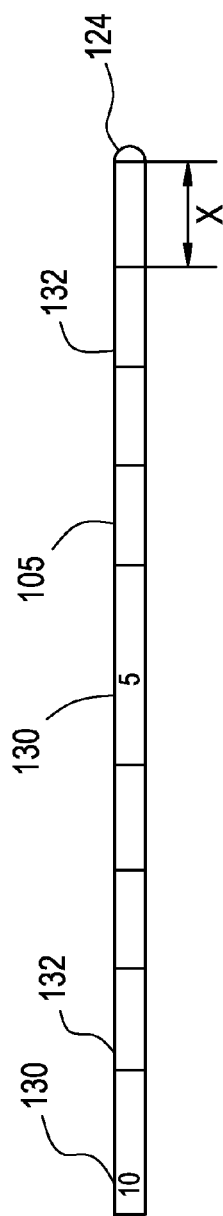
FIG. 3 is an elevational view of the distal portion of the esophageal mapping catheter of FIG. 2 in accordance with the present invention.

Referring to FIGS. 2-3, the esophageal mapping catheter 100 comprises a shaft 105 which is preferably a radiopaque Pellethane tube having a usable length 106 of approximately 125 centimeters sealed by an atraumatic tip made of a polyurethane (PU) dome 124 protecting the location sensor 120 at the distal end and closed by a handle 110 at the proximal end. The catheter materials are of sufficient stiffness to enable placement but are not so stiff as to cause mechanical damage to the tissues contacted during introduction and use. Although Pellethane is the preferable material for shaft 105 other materials may be used such as Silicone or other Polyurethane compounds compatible with the esophagus environment. The catheter 100 is sufficiently radiopaque to be uniquely identifiably under fluoroscopic visualization. Numerical distance markers 130 on the shaft 105 mark the distance in centimeters from the distal end of the catheter starting at 5 centimeters and increasing by 5 centimeters until approximately 120 centimeters at the proximal end. These markers assist the physician in determining if the esophageal mapping catheter 100 is in the desired position inside the esophagus of the patient. The catheter 100 is manufactured from materials compatible with the environment of the esophagus. The shaft 105 of the catheter is generally non-deflectable. The shaft 105 should be of sufficient reach length to achieve catheter tip positioning in the esophagus below the level of the heart.

Located at the proximal end of the catheter is a handle 110 with electrical connector 115 that connects to the PIU 200 via an interface cable (not shown). The hollow handle or handle housing 110 houses the printed circuit board (PCB) and associated microprocessor for storing and pre-processing the data collected from the location sensor 120. The interface cable is a standard cable terminated on both ends with multi-pin connectors such as that used with the Biosense Navistar® catheter. The interface cable connects to the PIU 200 of the electroanatomic mapping system enabling the user to record catheter tip location/orientation within the esophagus.

FIG. 3 depicts the distal portion 109 of catheter 100 which shows the numerical markers 130 and line makers 132 of shaft 105 in more detail. Line markers begin approximately 10 millimeters from the polyurethane dome 124 and are spaced at approximately every 10 millimeters (distance X) proximally from the distal end. Near the proximal end of the catheter 100 adjacent the distal end of handle 110 shaft 105 is covered by sleeves 107 and 108 which are heat shrink materials used to provide a transition between shaft 105 and intended to keep fluids from the interior of handle 110. Sleeves 107 and 108 are preferably made from Polyolefin, but may also be any flexible plastic that serves as a strain relief.

Figure 6:
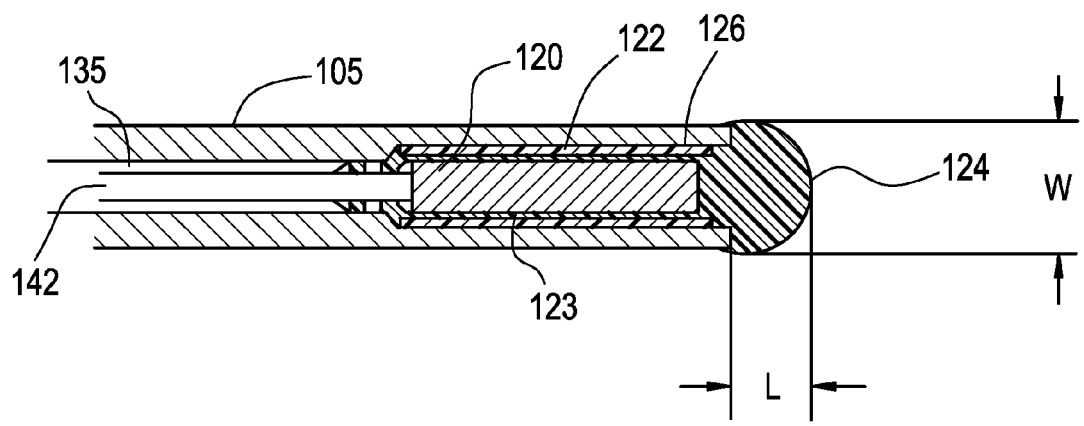
FIG. 6 is a longitudinal sectional view of the distal end of the esophageal mapping catheter of FIG. 2 in accordance with the present invention.

FIGS. 4-6 are longitudinal sectional view of the catheter 100 with the PCB subassembly 150 substantially surrounded by MU shield assembly 155. Electrical conductors 142 are connected (using solder, brazing or other electrical connection 151) to the circuitry on PCB subassembly 150. PCB subassembly 150 comprises the circuitry necessary to convert the electrical signals to from location sensor 120 from the analog format to a digital format and to generate a data format compatible with the format expected by the COM unit 210 as the data is sent to the anatomical mapping system 220. Electrical conductors 142 run through the central lumen 135 of shaft 105 and are connected at their distal end to location sensor 120.

As can bee seen in FIG. 5 which is a close-up of transition region 140, at the transition between shaft 105 and handle housing 110 transition sleeves 107 and 108 are sealed at the interface to the handle housing with a layer of polyurethane glue 114 which may be similar to the polyurethane used at distal tip 124. Sleeve 107 is approximately 2.0 inches in length and sleeve 108 is approximately 2.5 inches in length. Other sleeve arrangements may be used or alternatively shaft 105 could terminate within handle housing 110 and could be affixed within the handle housing with a polyurethane or other type of glue without using intermediary sleeves 107 and 108.

FIG. 6 is a close-up of the distal tip portion 109b of the catheter 100 of FIG. 4. Shaft 105 has a central lumen 135 in which electrical conductors 142 reside. Electrical conductors 142 are connected at their distal end to location sensor 120. Location sensor 120 is housed within a nylon zytel tube 122 which is held in place within shaft 105 by a layer of polyurethane glue 126 or other type of glue or cement. Location sensor 120 is held in place within tube 122 by a circumferential layer of polyurethane 123 which is capped by PU dome 124. PU dome 124 is approximately 0.10 to 0.12 inch in diameter at its widest portion (W) and is approximately 0.05 to 0.07 inches in length (L).

Figure 7:
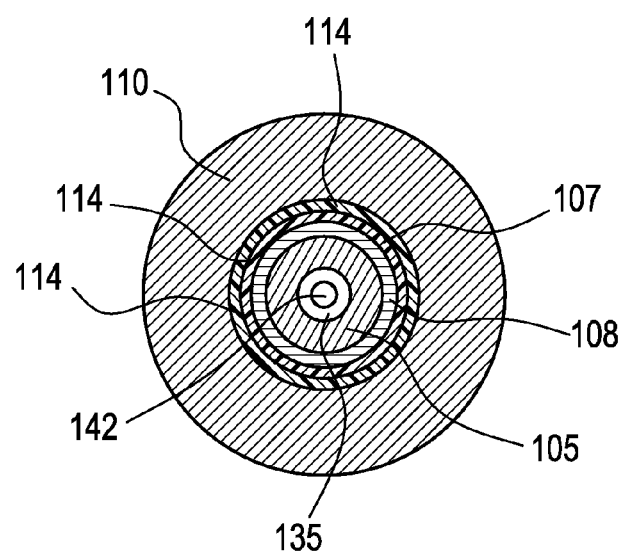
FIG. 7 is a cross-sectional view of the esophageal mapping catheter of FIG. 2 through line B-B.

FIG. 7 depicts the cross-sectional view of the esophageal mapping catheter in accordance with the present invention through line B-B of FIG. 2. Layers of polyurethane 114 can be used between sleeves 107 and 108 and shaft 105 in addition to the layer at the interface between the housing 110 and sleeve 107.

Figure 8:
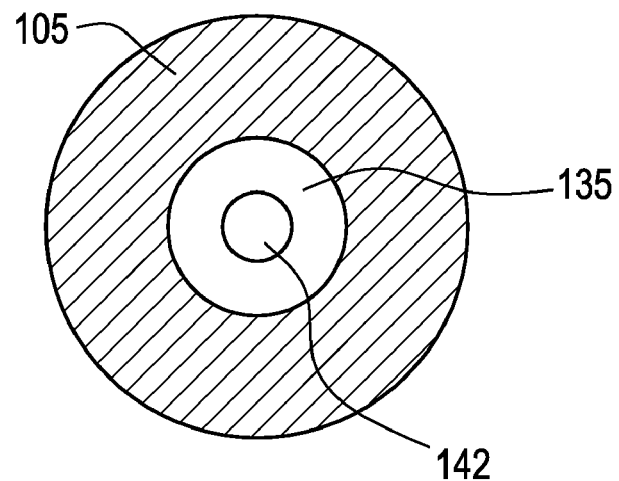
FIG. 8 is a cross-sectional view of the esophageal mapping catheter of FIG. 2 through line C-C.

FIG. 8 depicts the cross-sectional view of the esophageal mapping catheter of FIG. 2 through line C-C in the shaft region and shows the continuation of electrical conductors 142 through central lumen 135 of shaft 105.

Figure 9:
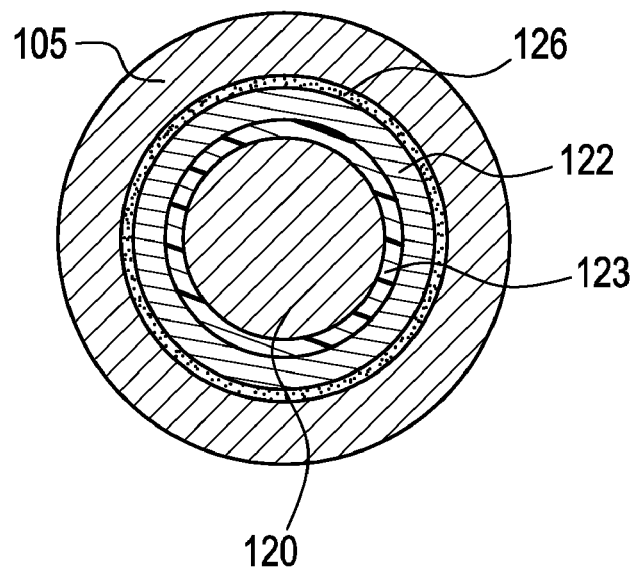
FIG. 9 is a cross-sectional view of the esophageal mapping catheter of FIG. 2 through line D-D.

FIG. 9 cross-sectional view of the esophageal mapping catheter of FIG. 2 through line D-D in the distal tip of the device. Position tracking is provided by a location sensor 120 that is located at the distal tip of the esophageal mapping catheter 100 and an external magnetic field (not shown). The location sensor 120 provides catheter tip location (x, y, z co-ordinates) as well as orientation (pitch, roll and yaw) information that is processed and displayed by the electroanatomic mapping system 220.

One embodiment of the esophageal mapping catheter 100 is 8 F in diameter with a usable length 106 of 125 cm although other diameters and lengths could be made. The catheter has a flexible polyurethane shaft 106 with an atraumatic tip section 124. Esophageal mapping catheter 100 has a magnetic location sensor 120 embedded in the distal tip that provides information to an electroanatomic mapping system such as the Carto™ EP Navigation System and a RefStar™ with QwikPatch™ External Reference Patch, which provides location information to construct a 3D electroanatomical map of the esophagus in real-time. The location sensor 120 provides catheter tip location (x, y, z co-ordinates) as well as orientation (pitch, roll and yaw) information that is processed and displayed by the electroanamtomic mapping system.

The esophageal mapping catheter 100 is used in conjunction with a navigational catheter, such as the NaviStar® Mapping and Ablation Catheter, to provide supplemental information for maps created with the navigational catheter and the electroanatomical mapping system. The esophageal mapping catheter 100 is intended to create esophageal reference points on the electroanatomical map in addition to the cardiac reference points created by the navigation catheter.

Figure 10:
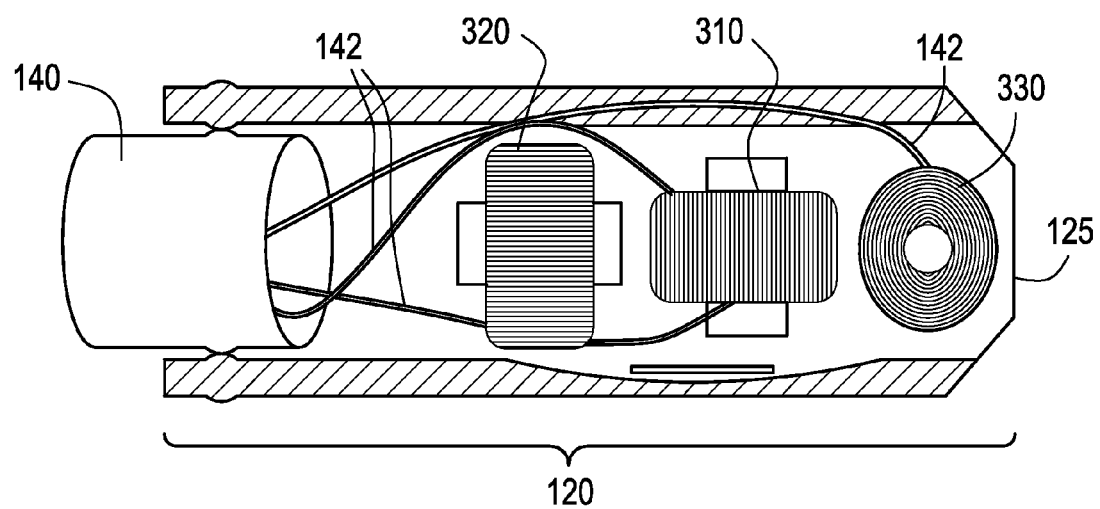
FIG. 10 is a diagram depicting the elements of the location sensor used in an esophageal mapping catheter in accordance with the present invention.

Referring to FIG. 10, the location sensor 120 for the esophageal mapping catheter 100 is similar or identical to the location sensors for known navigational catheters such as the NaviStar® navigational catheter. The sensor consists of three orthogonal miniature coils 310, 320 and 330 made from 10 μm copper wire wound around ferrite beads. Coil 310 provides information with respect to the x axis. Coil 320 provides information with respect to the y axis and coil 330 provides information with respect to the z axis. The ferrite beads serve to increase the location signal sensitivity in the coils of the sensor before reaching the pre-amplifier located on the PCB in the catheter handle 110. The coils 310, 320 and 330 are connected via electrical conductors 142 to the circuitry in handle 110. The coils comprising the sensor are contained within an epoxy/amide housing 125. It is embedded in the distal ends of the esophageal mapping catheter 100.

To account for patient movement, the location of the mapping catheter is referenced by the electroanatomical mapping system relative to the location of an external reference patch placed on the patient's back. The external reference patch has the same location sensor technology as the mapping catheter. The location information displayed on the screen of the electroanatomical mapping system is the location of the mapping sensor in space with the control for inappropriate movement of the mapping catheter relative to the location of the reference sensor.

Two mapping algorithms are used in the electroanatomical mapping system to convert the data received from the esophageal mapping catheter 100 and the reference patch into a 3D map include a triangulation algorithm for location and a reconstruction algorithm to create the 3-D map.

The underlying principle for the location algorithm is the same as the Global Positioning Systems (GPS) developed by the U.S. military and which is now in widespread commercial use for a variety of navigation functions. For example, an airplane can deduce its position by knowing the distance to three satellites, while the electroanatomical mapping system can deduce the position of the mapping catheter by knowing the distance to the three coils in the location pad. Each coil within the location sensor detects the intensity of the magnetic fields generated by each of the three location pad coils, allowing the determination of the distance. These distances determine the radii of theoretical spheres around each location pad coil. This information is used to determine three spatial coordinates (X, Y and Z) and three orientation parameters (roll, yaw and pitch). The electroanatomic mapping system then provides a visual display of the location of the sensors in space.

The electroanatomical mapping system records a set of points in a random manner. The map is reconstructed using an algorithm that chooses an ellipsoid (the smallest one containing all recorded points) as the initial shape and collapsing it around the fixed recorded points, until all points touch the surface of the reconstruction.

The esophageal mapping catheter 100 may also be placed within the esophagus behind the left atrium during an RF ablation procedure to measure the temperature inside the esophagus thereby providing user feedback in order to prevent thermal damage to the esophagus. Thermal information is provided by a thermal sensor co-located with the magnetic location sensor in the distal end of the esophageal mapping catheter 100. Thermal sensors of any known type may be used. Preferably the thermal sensor is Type T, made from Constantan and Copper wires.

A number of alternative 3D location recording technologies may be applicable to this concept e.g. impedance based location mapping. The esophageal mapping catheter 100 may be made so that it is deflectable. Esophageal mapping catheter 100 may be provided without thermocouples or lubricious coating. The esophageal mapping catheter may be provided with a balloon or cage mechanism to center the device in the esophagus. Esophageal mapping catheter 100 may be provided with electrode rings to record electrograms from within the esophagus.

In use by the physician or other user, the device is introduced into the esophagus via the throat or nasal passage and is aligned behind the heart using fluoroscopic guidance. Prior to performing left atrial (LA) ablations, the physician records location data points within the esophagus by advancing and withdrawing the device within the esophagus while recording catheter location information from the location sensor, tagging location points. The points serve to record device tip position within the esophagus, in turn recording the relative position of the esophagus with respect to the left atrium on the electroanatomic map. Esophagus points displayed on the electroanatomic map enable the physician to direct RF energy delivery away from the esophagus reducing the risk of esophageal fistula formation. In addition, the device can be placed within the esophagus, behind the left atrium, during RF energy delivery to measure esophagus temperatures. Esophagus temperature changes during ablation may provide the user feedback during the ablation to prevent thermal damage to the esophagus. The catheter placement in the esophagus can be guided using x-ray to insure that the radiopaque catheter aligns along the posterior wall of the left atrium. The device may be coated with a lubricious material such as PTFE or other such material to facilitate easy introduction into and manipulation within the esophagus. A hydrophilic coating may also be used to provide a device surface that eases introduction into the esophagus. Esophagus position information enables user to direct ablation away from the esophagus reducing risk of esophageal fistula formation. Temperature information may allow the user to control power delivery during ablation to prevent thermal damage to the esophagus.

For insertion into the esophagus, column strength is needed to avoid buckling or coiling of the device which may lead to an inability to advance the device pass the nasal passage or throat. This device stiffness can be accomplished through insertion of a stylet from an opening in the handle housing 110 through the central lumen 135 of shaft 105 up to near the distal tip. The stylet can be made of any material that is sufficiently stiff to provide pushability, such as stainless steel or other relatively low-cost but non-reactive material. Once in place in the esophagus, the stylet can be removed to return the device to a more flexible state.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for controlling an ablation of cardiac tissue using information regarding tissue temperature at various locations of an esophagus of a patient using an electroanatomic mapping system comprising the steps of:
   introducing an esophageal mapping catheter having a distal end into the esophagus of the patient wherein the distal end of the esophageal mapping catheter contains a location sensor having a plurality of coils, each coil capable of providing an electrical signal in response to a magnetic field;
   transmitting the plurality of electrical signals to the electroanatomic mapping system;
   generating a location of the distal end of the esophageal mapping catheter in the electroanatomic mapping system and displaying the location;
   withdrawing the distal end of the esophageal mapping catheter in order to generate location information along the internal surface of the esophagus;
   measuring the temperature at one or more locations along the internal surface of the esophagus; and,
   controlling an ablation of cardiac tissue near the esophagus based on the temperature within the esophagus.

2. The method of claim 1 where the esophageal mapping catheter further comprises a substantially tubular shaft wherein the location sensor resides near the distal end.

3. The method of claim 2 wherein the distal end of the esophageal mapping catheter is covered with an atraumatic tip.

4. The method of claim 3 wherein the atraumatic tip is polyurethane.

* * * * *